United States Patent [19]
Mahood

[11] Patent Number: 5,500,468
[45] Date of Patent: Mar. 19, 1996

[54] PROCESS FOR STABILIZING POLYMERIC MATERIAL

[75] Inventor: James A. Mahood, Morgantown, W. Va.

[73] Assignee: General Electric Company, Pittsfield, Mass.

[21] Appl. No.: 361,786

[22] Filed: Dec. 21, 1994

Related U.S. Application Data

[63] Continuation-in-part of Ser. No. 307,545, Sep. 16, 1994, Pat. No. 5,424,348, which is a continuation of Ser. No. 96,530, Jul. 22, 1993, abandoned.

[51] Int. Cl.$^6$ .................................................. C08K 5/527
[52] U.S. Cl. ............................................. 524/117; 526/78
[58] Field of Search ................................. 524/117; 526/78

[56] References Cited

U.S. PATENT DOCUMENTS

| | | |
|---|---|---|
| 2,957,747 | 10/1960 | Bowling. |
| 3,039,993 | 6/1962 | Friedman. |
| 3,056,823 | 10/1962 | Heckenbleikner et al.. |
| 3,264,247 | 8/1966 | Friedman. |
| 3,281,381 | 10/1966 | Hechenbleikner et al.. |
| 3,305,520 | 2/1967 | Fritz et al.. |
| 3,305,526 | 2/1967 | Guttag. |
| 3,342,767 | 9/1967 | Buckley. |
| 3,415,906 | 12/1968 | Shepard et al.. |
| 3,437,720 | 4/1969 | Guttag. |
| 3,441,633 | 4/1969 | Friedman. |
| 3,467,733 | 9/1969 | Dever et al.. |
| 3,482,002 | 12/1969 | Dever et al.. |
| 3,483,147 | 12/1969 | Friedman. |
| 3,488,407 | 1/1970 | Schall. |
| 3,509,091 | 4/1970 | Cleveland et al.. |
| 3,544,502 | 12/1970 | Boyer et al.. |
| 3,558,554 | 1/1971 | Kuriyama et al.. |
| 3,629,372 | 12/1971 | Drake. |
| 3,646,173 | 2/1972 | Gordon et al.. |
| 3,714,302 | 1/1973 | Dever et al.. |
| 3,794,629 | 2/1974 | Eimers et al.. |
| 3,824,205 | 7/1974 | Demarcq et al.. |
| 3,845,168 | 10/1974 | Guttag. |
| 3,855,164 | 12/1974 | Lohr, Jr. et al.. |
| 3,888,752 | 6/1975 | Eldred. |
| 4,000,221 | 12/1976 | Fodor. |
| 4,086,304 | 4/1978 | Hutton et al.. |
| 4,196,117 | 4/1980 | Spivack. |
| 4,318,845 | 3/1982 | Spivack et al.. |
| 4,405,739 | 9/1983 | Kinson. |
| 4,529,533 | 7/1985 | Chasar. |
| 4,661,545 | 4/1987 | Bruls et al.. |
| 4,708,979 | 11/1987 | Pedrazzetti et al.. |
| 4,755,546 | 7/1988 | Hechenbleikner et al.. |
| 4,782,170 | 11/1988 | Bae et al.. |
| 4,882,374 | 11/1989 | Wang et al.. |
| 4,956,406 | 9/1990 | Myers et al.. |
| 4,957,954 | 9/1990 | Iizuka et al.. |

FOREIGN PATENT DOCUMENTS

| | | |
|---|---|---|
| 2944254 | 5/1980 | Germany. |
| 2087399A | 5/1982 | United Kingdom. |

OTHER PUBLICATIONS

*Phosphorus and Sulfer,* 1983, vol. 15, pp. 9–13.

*Primary Examiner*—Veronica P. Hoke

[57] ABSTRACT

A polymerization process is provided involving a carrier solution containing an organic solvent and a phosphite. The phosphite is highly soluble in the solvent and allows for an incorporation of a minimum of solvent in the carrier sohltion. The phosphite is of the formula:

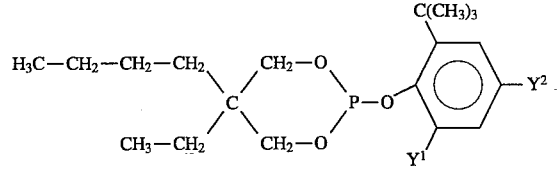

wherein $Y^1$ is an alkyl and $Y^2$ is selected from tert-butyl and sec-butyl. The process is useful for making polymers such as styrene-butadiene block copolymers which may then be molded to produce commercial articles or may be blended with other thermoplastics to enhance the impact strengths thereof.

13 Claims, No Drawings

PROCESS FOR STABILIZING POLYMERIC MATERIAL

This is a continuation-in-part of application Ser. No. 08/307,545 filed on Sep. 16, 1994 now U.S. Pat. No. 5,424,348, which is a continuation of 08/096,530, Jul. 22, 1993 abandoned.

BACKGROUND OF THE INVENTION

1. Field of the Invention

The present invention relates to solvent utilizing polymerization processes, and more particularly relates to solvent based delivery systems for phosphites.

2. DESCRIPTION OF RELATED ART

Solvent utilizing polymerization processes are generally known. Such processes are useful for manufacturing polymers such as homopolymers, block copolymers and graft copolymers, and include processes commonly referred to as bulk, mass, suspension and emulsion processes. Some of the processes attempt to incorporate antioxidants such as phosphites into the polymer material by introducing a solvent containing the antioxidant into the reaction process. These solvents generally need to be removed at some point in the process, and consequently there is at times a desire to minimize the amount of solvent in the process. Many phosphites, however, do not exhibit high levels of solubility in various organic solvents, for example, aliphatic or aromatic liquid (25° C.) hydrocarbons, for further example, cyclohexane.

Accordingly, there is a desire to provide a phosphite which exhibits high levels of solubility in organic solvents, and to provide a solvent delivery system for the phosphite which minimizes the amount of solvent required.

SUMMARY OF THE INVENTION

The present invention involves a polymerization process involving the delivery of a phosphite into the process via a solvent carrier, and further involves a solvent carrier solution containing a phosphite wherein the phosphite is of the formula:

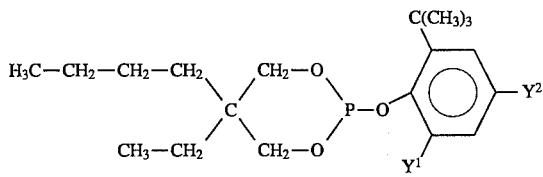

wherein $Y^1$ is an alkyl and $Y^2$ is selected from tert-butyl and sec-butyl. The solvent is an organic solvent.

DETAILED DESCRIPTION OF THE INVENTION

A process is provided for making polymeric materials. One embodiment of the process involves introducing a carrier solution into a reaction mass. The carrier solution contains an organic solvent and a phosphite that exhibits a high degree of solubility in the organic solvent.

The process is useful for making polymeric materials containing (desired from) diene compounds. The diene rubber polymers which can be used in the present invention are characterized by the following types (a) and (b): (a) ABA-type or ABA'-type copolymer (or their combination); (b) AB type di block copolymer.

In the aforementioned types, A and A' are blocks derived from comonomers consisting of unsaturated alkenyl aromatic compounds (e.g., styrene, α-methylstyrene, vinyltoluene, vinylxylene, vinylnaphthalene, etc.) or their mixtures, B is a block derived from comonomers consisting of diene compounds (e.g., butadiene, chlorobutadiene, isoprene, 1,3-pentadiene, 2,3-dimethylbutadiene, etc.) or their mixtures.

The ABA-type or ABA'-type copolymer may be a so-called "tapered" block copolymer, in which three blocks are directly connected to each other or via a "random copolymer" consisting of an alkenyl aromatic compound and a diene compound constituting each block, or a radial tele-block copolymer consisting of an alkenyl aromatic compound and a diene compound. The AB type di block copolymer is a "tapered" block copolymer in which two blocks are directly connected to one each other or via a "random copolymer" consisting of an alkenyl aromatic compound and a diene compound constituting each block.

Examples of especially desirable rubber polymers corresponding to the aforementioned type (a) include a styrene-ethylene-butadiene-styrene block copolymer, styrene-butadiene-styrene block copolymer, styrene-isoprene-styrene block copolymer, etc. Examples of especially rubber polymers corresponding to the aforementioned type (b) include a styrene-ethylene-propylene block copolymer, styrene-butadiene block copolymer, etc.

The aforementioned rubber polymers may be totally hydrogenated, partially hydrogenated, or acid-modified using maleic anhydride, etc. In particular, hydrogenated polymers are especially desirable in consideration of the thermal ageing resistance.

It is desirable that the quantity of rubber polymer content be 1–80 parts by weight (with respect to 100 parts by weight) of the resin composition of the present invention. Then, it is desirable that the relative quantities of components (a) and (b) be 3–97 wt % and 97–3-wt %, respectively.

If necessary, furthermore, other rubbers (e.g., ethylene-propylene rubber, etc.) may be used in combination with the aforementioned rubber polymers of components (a) and (b).

The process is also useful for making graft copolymer having a diene rubber component. Rubber modified monovinylidene aromatic resins comprising (a) a rubber modified monovinylidene aromatic graft copolymer and (b) an ungrafted rigid copolymer, are generally prepared by graft polymerization of a mixture of a monovinylidene aromatic monomer and one or more comonomers in the presence of one or more rubbery polymeric substrates. Depending on the amount of rubber present, a separate matrix or continuous rigid phase of ungrafted rigid (co)polymer may be simultaneously obtained along with the rubber modified monovinylidene aromatic graft polymer. The resins may also be produced by blending a rigid monovinylidene aromatic copolymer with one or more rubber modified monovinylidene aromatic graft copolymers. Typically, the rubber modified resins comprise the rubber modified graft copolymer at a level of from 5 to 100 percent by weight based on the total weight of the resin, more preferably from 10 to 95 percent by weight thereof, more preferably 20 to 90 percent by weight thereof, and most preferably from 15 to 85 percent by weight thereof; and the rubber modified resin comprises the ungrafted rigid polymer at a level of from 0 to 95 percent by weight based on the total weight of the resin, more preferably from 5 to 90 percent by weight thereof, more preferably from 10 to 80 percent by weight thereof and most preferably from 15 to 85 percent by weight thereof.

Monovinylidene aromatic monomers which may be employed include styrene, alpha-methyl styrene, halostyrenes i.e. dibromostyrene, mono or di alkyl, alkoxy or hydroxy substitute groups on the nuclear ring of the monovinylidene aromatic monomer i.e. vinyl toluene, vinylxylene, butylstyrene, parahydroxystyrene or methoxystyrene or mixtures thereof. The monovinylidenearomatic monomers utilized are generically described by the following formula:

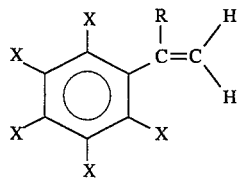

wherein X is selected from the group consisting of hydrogen, alkyl groups of 1 to 5 carbon atoms, cycloalkyl, aryl, alkaryl, aralkyl, alkoxy, aryloxy, and halogens. R is selected from the group consisting of hydrogen, alkyl groups of 1 to 5 carbon atoms and halogens such as bromine and chlorine. Examples of substituted vinylaromatic compounds include styrene, 4-methylstyrene, 3,5-diethylstyrene, 4-n-propylstyrene, α-methylstyrene, α-methyl vinyltoluene, α-chlorostyrene, α-bromostyrene, dichlorostyrene, dibromostyrene, tetrachlorostyrene, mixtures thereof and the like. The preferred monovinylidene aromatic monomers used are styrene and/or α-methylstyrene.

Comonomers which may be used with the monovinylidene aromatic monomer includes acrylonitrile, methacrylonitrile, $C_1$ to $C_8$ alkyl or aryl substituted acrylate, $C_1$ to $C_8$ alkyl, aryl or haloaryl substituted methacrylate, acrylic acid, methacrylic acid, iraconic acid, acrylamide, N-substituted acrylamide or methacrylamide, maleic anhydride, maleimide, N-alkyl, aryl or haloaryl substituted maleimide, glycidyl (meth)acrylates, hydroxy alkyl (meth)acrylates or mixtures thereof. The acrylonitrile, substituted acrylonitrile, or acrylic acid esters are described generically by the following formula:

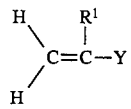

wherein $R^1$ may be selected from the same group set out for R as previously defined and Y is selected from the group consisting of cyano and carbalkoxy groups wherein the alkoxy group of the carbalkoxy contains from one or about twelve carbon atoms. Examples of such monomers include acrylonitrile, ethacrylonitrile, methacrylonitrile, α-chloroacrylonitrile, α-bromoacrylonitrile, methyl acrylate, methyl methacrylate, ethyl acrylate, butyl acrylate, propylacrylate, isopropyl acrylate and mixtures thereof. The preferred monomer is acrylonitrile and the preferred acrylic acid esters are ethyl acrylate and methyl methacrylate. It is also preferred that the acrylic acid esters, when included, are employed in combination with styrene or acrylonitrile.

The rubber modified graft copolymer comprises (i) the rubber substrate, and (ii) a rigid polymeric superstrate portion grafted to the rubber substrate. The rubber substrate is preferably present in the graft copolymer at a level of from 5 to 85 percent by weight based on the total weight of the graft copolymer, more preferably from 10 to 80 percent by weight thereof, and most preferably 20 to 70 percent by weight thereof; and the rigid superstrate is preferably present at a level of from 15 to 95 percent by weight based on the total weight of the graft copolymer, more preferably from 20 to 90 percent by weight thereof, and most preferably from 30 to 80 percent by weight thereof.

For high rubber graft emulsion resins, the rubber level will range from 50 to 85% by weight based on the total weight of the rubber modified resin. For mass polymerization, the rubber level ranges from 4 to 40% by weight based on the total weight of the rubber modified resin. For blends of an ungrafted rigid copolymer (such as styreneacrylonitrile copolymer) with an emulsion high rubber graft (HRG) copolymer (such as acrylonitrile-butadiene-styrene graft copolymers), the rubber loading will typically range from 10 to 40% rubber based on the total weight of the rubber modified resin.

Examples of rubbery polymers for the substrate include: conjugated dienes, copolymers of a diene with styrene, acrylonitrile, methacrylonitrile or $C_1$ to $C_8$ alkyl acrylate which contain at least 50% (preferably at least 65% by weight) conjugated dienes, polyisoprene or mixtures thereof; olefin rubbers i.e. ethylene propylene copolymer (EPR) or ethylene propylene non-conjugated diene (EPDM); silicone rubbers; or $C_1$ or $C_8$ alkyl acrylate homopolymers or copolymers with butadiene and/or styrene. The acrylic polymer may also contain up to 5% of one or more polyfunctional crosslinking agents such as alkylenediol di(meth)acrylates, alkylenetriol tri(meth)acrylates, polyester di(meth)acrylates, divinylbenzene, trivinylbenzene, butadiene, isoprene and optionally graftable monomers such as, triallyl cyanurate, triallyl isocyanurate, allyl (meth)acrylate, diallyl maleate, diallyl fumarate, diallyl adipate, triallyl esters of citric acid or mixtures of these agents.

The diene rubbers may preferably be polybutadiene, polyisoprene and copolymers of butadiene with up to 35% by weight of comonomers such as styrene, acrylonitrile, methylmethacrylate or $C_1$-$C_6$-alkylacrylate which are produced by aqueous radical emulsion polymerisation. The acrylate rubbers may be cross-linked, particulate emulsion copolymers substantially of $C_1$-$C_8$-alkylacrylate, in particular $C_2$-$C_6$-alkylacrylate, optionally in admixture with up to 15% by weight of comonomers such as styrene, methylmethacrylate, butadiene, vinyl methyl ether or acrylonitrile and optionally up to 5% by weight of a polyfunctional crosslinking comonomer, e.g. divinylbenzene, glycol-bis-acrylates, bisacrylamides, phosphoric acid triallylester, citric acid triallylester, allylesters of acrylic acid or methacrylic acid, triallylcyanurate, triallylisocyanurate. Also suitable are mixtures of diene- and alkylacrylate rubbers and rubbers which have a so-called core/sheath structure, e.g. a core of diene rubber and a sheath of acrylate or vice versa.

Specific conjugated diene monomers normally utilized in preparing the rubber substrate of the graft polymer are generically described by the following formula:

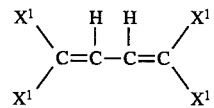

wherein $X^1$ is selected from the group consisting of hydrogen, alkyl groups containing from one to five carbon atoms, chlorine or bromine. Examples of dienes that may be used are butadiene, isoprene, 1,3-heptadiene, methyl-1,3-pentadiene, 2,3-dimethylbutadiene, 2-ethyl-1,3-pentadiene 1,3- and 2,4-hexadienes, chloro and bromo substituted butadienes such as dichlorobutadiene, bromobutadiene, dibromobutadiene, mixtures thereof, and the like. A preferred conjugated diene is 1,3 butadiene.

The substrate polymer, as mentioned, is preferably a conjugated diene polymer such as polybutadiene, polyisoprene, or a copolymer, such as butadiene-styrene, butadiene-acrylonitrile, or the like. The rubbery polymeric substrate portion must exhibit a glass transition temperature (Tg) of less than about 0° C.

Mixtures of one or more rubbery polymers previously described for preparing the monovinylidene aromatic graft polymers, or mixtures of one or more rubber modified monovinylidene aromatic graft polymers disclosed herein may also be employed. Furthermore, the rubber may comprise either a block or random copolymer. The rubber particle size used in this invention as measured by simple light transmission methods or capillary hydrodynamic chromatography (CHDF) may be described as having an average particle size by weight of select one of the following: 0.05 to 1.2 microns, preferably 0.2 to 0.8 microns, for emulsion based polymerized rubber latices or 0.5 to 10 microns, preferably 0.6 to 1.5 microns, for mass polymerized rubber substrates which also have included grafted monomer occlusions. The rubber substrate is preferably a particulate, highly crosslinked diene or alkyl acrylate rubber, and preferably has a gel content greater than 70%.

Preferred graft superstrates include copolymers of styrene and acrylonitrile, copolymers of α-methylstyrene and acrylonitrile and methylmethacrylate polymers or copolymers with up to 50% by weight of $C_1$–$C_6$ alkylacrylates, acrylonitrile or styrene. Specific examples of monovinylidene aromatic graft copolymers include but are not limited to the following: acrylonitrile-butadiene-styrene (ABS), acrylonitrile-styrene-butyl acrylate (ASA), methylmethacrylate-acrylonitrile-butadiene-styrene (MABS), acrylonitrile-ethylene-propylene-nonconjugated diene-styrene (AES).

The ungrafted rigid polymers (typically free of rubber) are resinous, thermoplastic polymers of styrene, α-methylstyrene, styrenes substituted in the nucleus such as ρ-methylstyrene, methyl acrylate, methylmethacrylate, acrylonitrile, methacrylonitrile, maleic acid anhydride, N-substituted maleimide, vinyl acetate or mixtures thereof. Styrene/acrylonitrile copolymers, α-methylstyrene/acrylonitrile copolymers and methylmethacrylate/acrylonitrile copolymers are preferred.

The ungrafted rigid copolymers are known and may be prepared by radical polymerisation, in particular by emulsion, suspension, solution or bulk polymerisation. They preferably have number average molecular weights of from 20,000 to 200,000 and limiting viscosity numbers [η] of from 20 to 110 ml/g (determined in dimethylformamide at 25° C.).

The number average molecular weight of the grafted rigid superstrate of the monovinylidene aromatic resin is designed to be in the range of 20,000 to 350,000. The ratio of monovinylidene aromatic monomer to the second and optionally third monomer may range from 90/10 to 50/50 preferably 80/20 to 60/40. The third monomer may optional replace 0 to 50% of one or both of the first and second monomers.

These rubber modified monovinylidene aromatic graft polymers may be polymerized either by mass, emulsion, suspension, solution or combined processes such as bulk-suspension, emulsion-bulk, bulk-solution or other techniques well known in the art. Furthermore, these rubber modified monovinylidene aromatic graft copolymers may be produced either by continuous, semibatch or batch processes.

The organic solvent may be any suitable organic solvent, which preferably has a melt temperature below 25° C., and suitable examples include $C_3$ to $C_{20}$ hydrocarbons, more preferably $C_4$ to $C_{10}$ hydrocarbons, such as benzene, tetrahydrofuran, dioxane, 1,2-dimethoxyethane and n-hexane, and most preferably is cyclohexane. Other suitable solvents include aliphatic or aromatic hydrocarbons, mineral oil, and hydrocarbon monomers such as styrene. The carrier solution is a solution of organic solvent and phosphite. The phosphite is preferably present at a level of from 1 to 50 percent by weight based on the total weight of the carrier solution, more preferably from 10 to 50 percent by weight thereof, and most preferably from 20 to 40 percent by weight thereof. The organic solvent is preferably present in the carrier solution at a level of from 50 to 99 percent by weight based on the total weight of the carrier solution, more preferably from 50 to 90 percent by weight thereof, and most preferably from 60 to 80 percent by weight thereof.

One embodiment of the process involves feeding the carrier solution into a reaction mass. The reaction mass comprises vinyl monomers and diene monomers and/or diene derived polymers. The phosphite serves to enhance the oxidative stability of the polymeric materials during processing and post-processing. Another embodiment of the process involves introducing the carrier solution into the polymeric material, and then removing the solvent therefrom.

Other suitable processes for using the present invention include processes for making vinylic polymers including, for example, polystyrene, polyvinylchloride, anionic polymers, polybutadiene, polyisoprene, and polymethylmethacrylate.

Mass, bulk, mass-suspension, suspension and emulsion processes are well known in the art. The present invention involves improving the phosphite delivery system of those processes by utilizing a carrier solution that contains a phosphite which exhibits high levels of solubility in organic solvents.

Polymeric material as used herein refers to either the final polymer product or the final polymeric product in solution or dispersion.

The phosphite preferably has a melt temperature above 25° C.

TABLE 1

| Ex | Phos | Solubility % |
|----|------|--------------|
| 1  | Phos 1 | 50.1 |
| A  | Phos A | <10 |
| B  | Phos B | 15.7 |
| C  | Phos C | 12.4 |

Solubility for example 1 and comparative example A is measured as solubility in hexane with each percentage value being equal to grams of phos per milliliter of hexane (20%=2 g/ml, 10%=1 g/ml.

Phos A is Tetrakis(2,4-di-tert-butylphenyl)4,4'-diphenylylenediphosphonite.

Phos 1 is of the formula

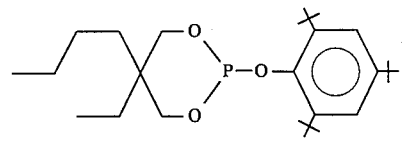

The examples of Table 2 illustrate the in polymer solubility of the present phosphites which should facilitate phosphite dispersion in the polymer compositions.

Phos B is bis(2,4-di-t-butylphenyl) pentaerythritol diphosphite.

Phos C is tris(2,4-di-tert-butylphenyl) phosphite.

Phos D is trisnonylphenyphosphite.

CEX D-G were comparative examples and examples 2 and 3 were examples of the present invention.

Phos 2 was of the formula

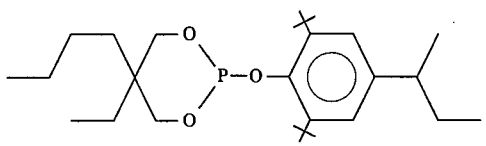

Values are set out as concentration in parts per million based on the total weight of the linear low density polyethylene. The greatly increasing values with time for examples 2 and 3 compared to CEX D-G illustrates the greatly enhanced solubility of the present phosphites.

TABLE 2

| Time (Weeks) | CEXD Phos B | CEXE Phos C | CEXF Phos D | CEXG Phos A | EX2 Phos 1 | EX3 Phos2 |
| --- | --- | --- | --- | --- | --- | --- |
| 0 | 0 | 0 | 0 | 0 | 0 | 0 |
| 1 | — | — | — | — | 275 | 1171 |
| 3 | — | — | 394 | — | 1177 | 4366 |
| 5 | 35 | 33 | 789 | 97 | 1595 | 6375 |
| 7 | 99 | 41 | 1204 | 291 | 1992 | 8151 |
| 9 | 59 | 95 | 773 | 320 | 2269 | 9037 |
| 11 | 111 | 40 | 777 | — | 2791 | — |
| 13 | 114 | 37 | — | — | 2348 | 9007 |
| 15 | 77 | 33 | 1003 | 365 | 2187 | 8971 |

I claim:

1. A polymerization process comprising:
   (a) introducing a carrier solution into a vinylic monomeric reaction mass, said carrier solution comprising a liquid organic solvent and a phosphite of the formula:

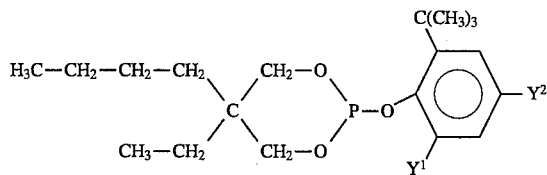

wherein $Y^1$ is an alkyl and $Y^2$ is selected from tert-butyl and sec-butyl,
   (b) polymerizing said monomeric reaction mass to produce a phosphite stabilized polymeric material.
2. The process of claim 1 wherein said solvent is removed from said polymeric material.
3. The process of claim 1 wherein said reaction mass comprised a diene compound.
4. The process of claim 1 wherein said reaction mass comprises a vinyl aromatic monomer.
5. The process of claim 1 wherein said polymeric material comprises vinyl aromatic-diene copolymers.
6. The process of claim 5 wherein said copolymer is a styrene-butadiene-styrene block copolymer.
7. A carrier solution for introducing a phosphite into a reaction mass of a polymerization process, said carrier solution comprising:
   (a) an organic solvent, and
   (b) a phosphite of the formula

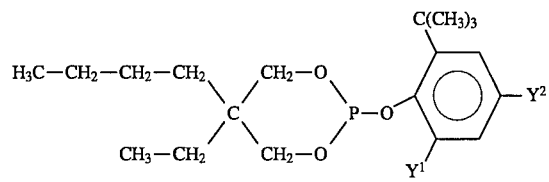

wherein $Y^1$ is an alkyl and $Y^2$ is selected from tert-butyl and sec-butyl.
8. The carrier solution of claim 7 wherein said solvent is cyclohexane.
9. The carrier solution of claim 7 wherein $Y^1$ and $Y^2$ are each tert-butyl.
10. The carrier solution of claim 7 wherein said phosphite is present at a level of from 1 to 50 percent by weight based on the total weight of the composition.
11. The carrier solution of claim 7 wherein said phosphite is present at a level of from 2 to 25 percent by weight based on the total weight of the composition.
12. The carrier solution of claim 7 wherein said phosphite is present at a level of from 2 to 15 percent by weight based on the total weight of the composition.
13. A polymerization process comprising:
   (a) polymerizing a vinylic monomeric reaction mass to produce a polymeric material;
   (b) introducing a carrier solution into said polymeric material, said carrier solution comprising a liquid organic solvent and a phosphite of the formula:

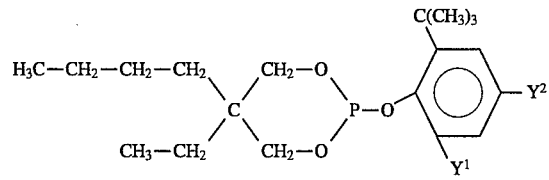

wherein $Y^1$ is an alkyl and $Y^2$ is selected from tert-butyl and sec-butyl.

* * * * *